United States Patent

Lang et al.

Patent Number: 5,114,955
Date of Patent: May 19, 1992

[54] SUBSTITUTED THIENOIMIDAZOLE DERIVATIVES

[75] Inventors: Hans-Jochen Lang, Hofheim am Taunus; Klaus Weidmann, Kronberg/Taunus; Karl-Heinz Scheunemann; Hildegard Nimmesgern, both of Frankfurt am Main; Robert Rippel, Hofheim am Taunus; Andreas W. Herling, Bad Camberg, all of Fed. Rep. of Germany

[73] Assignee: Hoechst Aketiengesellschaft, Frankfurt am Main, Fed. Rep. of Germany

[21] Appl. No.: 269,285

[22] Filed: Nov. 10, 1988

[30] Foreign Application Priority Data

Nov. 13, 1987 [DE] Fed. Rep. of Germany ...... 3738520
Jun. 4, 1988 [DE] Fed. Rep. of Germany ...... 3819084
Aug. 19, 1988 [DE] Fed. Rep. of Germany ...... 3828158

[51] Int. Cl.⁵ .................. A61K 31/44; C07D 405/14
[52] U.S. Cl. .................................. 514/338; 546/271
[58] Field of Search ....................... 546/271; 514/338

[56] References Cited

U.S. PATENT DOCUMENTS 4,845,118  7/1989  Lang et al. .................. 514/388

FOREIGN PATENT DOCUMENTS

86/57164  11/1986  Australia.
1262731  11/1989  Canada.
1234058  6/1971  United Kingdom.

Primary Examiner—Jane T. Fan
Attorney, Agent, or Firm—Finnegan, Henderson, Farabow, Garrett and Dunner

[57] ABSTRACT

Substituted thienoimidzaole derivatives, processes for their preparation, pharmaceutical preparations containing them and their use as inhibitors of gastric acid secretion.

The invention relates to substituted thienoimidazole derivatives of the formula

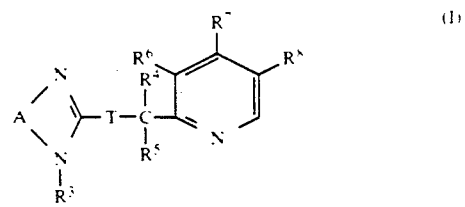

in which
A stands for

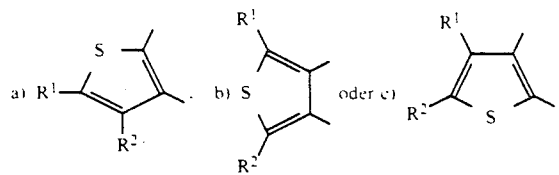

T denotes —S—, —SO— or —SO$_2$—,
R$^7$ denotes a substituted aryloxy or aralkoxy radical and R$^1$, R$^2$, R$^3$, R$^4$, R$^5$, R$^6$ and R$^8$ have the meanings indicated in the description, processes for their preparation, pharmaceutical preparations containing them and their use as medicaments.

15 Claims, No Drawings

SUBSTITUTED THIENOIMIDAZOLE DERIVATIVES

Thienoimidazole derivatives having gastric acid secretion-inhibiting action have been disclosed in EP-A1-234,485, EP-A2-201,094 and EP-A-237,248.

The present invention relates to novel thienoimidazole derivatives of the formula I

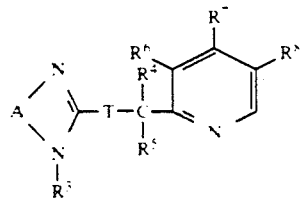

in which
A stands for

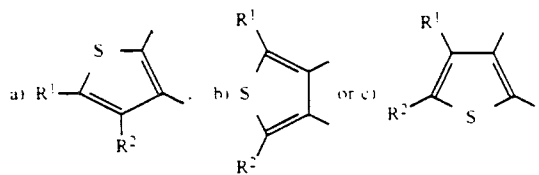

T denotes —S—, —SO— or —SO$_2$—.

R$^1$ and R$^2$ are identical or different and denote hydrogen, halogen, cyano, nitro, trifluoromethyl, (C$_1$-C$_6$)-alkyl, (C$_1$-C$_6$)-hydroxyalkyl, (C$_1$-C$_6$)-alkoxy, —O—[CH$_2$—]$_x$C$_f$H$_{(2f-1-g)}$F$_g$, —OCF$_2$Cl, —O—CF$_2$—CHFCl, (C$_1$-C$_6$)-alkylmercapto, (C$_1$-C$_6$)-alkylsulfinyl, (C$_1$-C$_6$)-alkylsulfonyl, (C$_1$-C$_6$)-alkylcarbonyl, (C$_1$-C$_6$)-alkoxycarbonyl, carbamoyl, N-(C$_1$-C$_4$)-alkylcarbamoyl, N,N-di-(C$_1$-C$_4$)-alkylcarbamoyl, (C$_1$-C$_6$)-alkylcarbonyloxy, (C$_3$-C$_8$)-cycloalkyl, phenyl, benzyl, phenoxy, benzyloxy, anilino, N-methylanilino, phenylmercapto, phenylsulfonyl, phenylsulfinyl, sulfamoyl, N-(C$_1$-C$_4$)-alkylsulfamoyl or N,N-di(C$_1$-C$_4$)-alkylsulfamoyl, or, if A is as defined above under (a) or (c), can also together denote —[CH$_2$]$_n$— or —CH=CH—CH=CH—, in which a CH$_2$ group is optionally replaced by O, S, SO or SO$_2$, or R$^3$ denotes hydrogen, (C$_1$-C$_6$)-alkanoyl, (C$_1$-C$_6$)-alkylcarbamoyl, (C$_1$-C$_6$)-alkoxycarbonyl, benzyloxycarbonyl or another physiologically tolerable N$^{im}$ protecting group which can preferably be cleaved in acidic medium and/or under physiological conditions such as, for example, (C$_1$-C$_{10}$)-acyloxy-(C$_1$-C$_6$)-alkyl, preferably (C$_1$-C$_{10}$)-alkanoyloxy-(C$_1$-C$_6$)-alkyl, benzoyloxy-(C$_1$-C$_6$)-alkyl, benzyloxycarbonyloxy-(C$_1$-C$_6$)-alkyl or (C$_1$-C$_6$)-alkoxycarbonyloxy-(C$_1$-C$_6$)-alkyl, R$^4$ and R$^5$ are identical or different and denote hydrogen or (C$_1$-C$_3$)-alkyl, R$^6$ and R$^8$ are identical or different and denote hydrogen, halogen, trifluoromethyl, (C$_1$-C$_{12}$)-alkyl, (C$_1$-C$_{12}$)-alkoxy, —O—[CH$_2$—]$_x$C$_f$H$_{(2f-1-g)}$F$_g$, —NR'R'', (C$_1$-C$_{12}$)-alkoxy-(C$_1$-C$_{12}$)-alkyl, (C$_1$-C$_{12}$)-alkoxy-(C$_1$-C$_{12}$)-alkoxy, (C$_7$-C$_{11}$)-aralkoxy, (C$_1$-C$_{12}$)-alkylmercapto, (C$_1$-C$_{12}$)-alkylsulfinyl or (C$_1$-C$_{12}$)-alkylsulfonyl, R$^7$ denotes a substituted (C$_6$-C$_{12}$)-aryloxy radical or (C$_7$-C$_{11}$)-aralkoxy radical which carries 1, 2, 3, 4 or 5 identical or different substituents selected from the group comprising halogen, cyano, nitro, trifluoromethyl, (C$_1$-C$_6$)-alkyl, (C$_1$-C$_6$)-hydroxyalkyl, (C$_1$-C$_6$)-alkoxy, —O—[CH$_2$—]$_x$C$_f$H$_{(2f-1-g)}$F$_g$, —OCF$_2$Cl, —O—CF$_2$—CHFCl, (C$_1$-C$_6$)-alkylmercapto, (C$_1$-C$_6$)-alkylsulfinyl, (C$_1$-C$_6$)-alkylsulfonyl, (C$_1$-C$_6$)-alkylcarbonyl, (C$_1$-C$_6$)-alkoxycarbonyl, carbamoyl, N-(C$_1$-C$_4$)-alkylcarbamoyl, N,N-di-(C$_1$-C$_4$)-alkylcarbamoyl, (C$_1$-C$_6$)-alkylcarbonyloxy, (C$_3$-C$_8$)-cycloalkyl, phenyl, benzyl, phenoxy, benzyloxy, NR'R'', phenylmercapto, phenylsulfonyl, phenylsulfinyl, sulfamoyl, N-(C$_1$-C$_4$)-alkylsulfamoyl or N,N-di(C$_1$-C$_4$)-alkylsulfamoyl, or which optionally carries up to 3 of the previously mentioned identical or different substituents and two adjacent carbon atoms of the aralkoxy radical together carry a —[CH$_2$—]$_n$ or —CH=CH—CH=CH— chain, in which one CH$_2$ group of the chain is optionally replaced by O, S, SO, SO$_2$ or NR'.

R$^5$ and R$^6$ together stand for —[CH$_2$]$_i$— and R$^4$, R$^7$ and R$^8$ are as defined above.

R' and R'' are identical or different and denote hydrogen, (C$_6$-C$_{12}$)-aryl or (C$_1$-C$_8$)-alkyl, or R' and R'' together stand for —[CH$_2$]$_h$—, in which a CH$_2$ group can be replaced by O, S, N-(C$_1$-C$_4$)-alkanoylimino or N-(C$_1$-C$_4$)-alkoxycarbonylimino.

f is 1, 2, 3, 4, 5, 6, 7 or 8, preferably 1 to 5,
g is 0, 1 to (2f+1),
h is 3, 4, 5 or 6,
i is 1, 2, 3 or 4,
n is 3 or 4,
x is 0, 1, 2 or 3, preferably 0 or 1,
and their physiologically tolerable salts.

1H-Thieno[3,4-d]imidazole derivatives of the formula I, in which A is as defined above under (b), are preferred. T is preferably an —SO— group.

R$^7$ preferably stands for a substituted phenylalkoxy radical of the formula

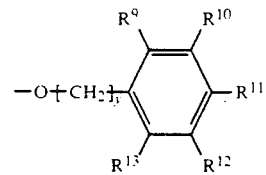

in which R$^9$, R$^{10}$, R$^{11}$, R$^{12}$ and R$^{13}$ are identical or different and denote hydrogen, halogen, cyano, nitro, trifluoromethyl, (C$_1$-C$_6$)-alkyl, (C$_1$-C$_6$)-alkoxy, —O—[CH$_2$—]$_x$C$_f$H$_{(2f-1-g)}$F$_g$, —OCF$_2$Cl, —O—CF$_2$—CHFCl, (C$_1$-C$_6$)-alkylmercapto, (C$_1$-C$_6$)-alkylsulfinyl, (C$_1$-C$_6$)-alkylsulfonyl, (C$_1$-C$_6$)-alkylcarbonyl, (C$_1$-C$_6$)-alkoxycarbonyl, carbamoyl, N-(C$_1$-C$_4$)-alkylcarbamoyl, N,N-di(C$_1$14 C$_4$)-alkylcarbamoyl, (C$_1$-C$_6$)-alkylcarbonyloxy, (C$_3$-C$_8$)-cycloalkyl, phenyl, benzyl, phenoxy, benzyloxy, NR'R'', such as amino, anilino, N-methylanilino, phenylmercapto, phenylsulfonyl, phenylsulfinyl, sulfamoyl, N-(C$_1$-C$_4$)-alkylsulfamoyl or N,N-di-(C$_1$-C$_4$)-alkylsulfamoyl, or two adjacent substituents together denote a —[CH$_2$—]$_n$ or —CH=CH—CH=CH— chain, in which one CH$_2$ group of the chain is optionally replaced by O, S, SO, SO$_2$ or NR', y denotes 0, 1, 2, 3 or 4, preferably 0 and 1, and the remaining substituents R$^9$, R$^{10}$, R$^{11}$, R$^{12}$ and R$^{13}$ are as defined previously, where unsubstituted benzyloxy and unsubstituted phenoxy are excluded. and R', R'', f, g, n and x are as defined above.

Particularly preferred compounds of the formula I are those in which

A is preferably as defined above under b).

T preferably denotes an —SO— group.

$R^1$ and $R^2$ are identical or different and denote hydrogen. ($C_1$-$C_3$)-alkyl, halogen, ($C_1$-$C_4$)-alkoxy, —O—[$CH_2$—]$_x C_yH_{(2y-1-g)}F_g$ or ($C_1$-$C_4$)-alkoxycarbonyl.

$R^3$ is as defined above.

$R^4$ and $R^5$ each denote hydrogen.

$R^6$ and $R^8$ are identical or different and denote hydrogen, halogen, ($C_1$-$C_3$)-alkyl, ($C_1$-$C_6$)-alkoxy and a fluoroalkoxy radical of the formula —O—[$CH_2$—]$_x C_yH_{(2y-1-g)}F_g$.

$R^7$ denotes a monosubstituted or polysubstituted benzyloxy or phenoxy radical.

$R^9$, $R^{10}$, $R^{11}$, $R^{12}$ and $R^{13}$ are identical or different and denote hydrogen, fluorine, chlorine, bromine, trifluoromethyl, cyano, nitro, ($C_1$-$C_6$)-alkoxycarbonyl and the remaining radicals and variables are as defined above.

in particular, however, compounds of the formula I, in which

A is preferably as defined above under (b).

T preferably denotes an —SO— group.

$R^1$ and $R^2$ are identical or different and denote hydrogen or ($C_1$-$C_3$)-alkyl.

$R^3$ is as defined above.

$R^4$ and $R^5$ each denote hydrogen.

$R^6$ and $R^8$ are identical or different and denote hydrogen, ($C_1$-$C_3$)-alkyl or ($C_1$-$C_3$)-alkoxy.

$R^7$ denotes a monosubstituted or polysubstituted benzyloxy or phenoxy radical.

$R^9$, $R^{10}$, $R^{11}$, $R^{12}$ and $R^{13}$ are identical or different and denote hydrogen, fluorine, chlorine, trifluoromethyl and the remaining radicals and variables are as defined above.

The following are of particular significance:

2-[4-(4-trifluoromethylbenzyloxy)-2-picolyl-sulfinyl]-1H-thieno[3,4-d]imidazole

2-[3-methoxy-4-(4-trifluoromethylbenzyloxy)-2-picolylsulfinyl]-1H-thieno[3,4-d]imidazole 2-[3-methoxy-4-(4-fluorobenzyloxy)-2-picolylsulfinyl]-1H-thieno[3,4-d]imidazole 2-[4-(3,5-bistrifluoromethylbenzyloxy)-2-picolylsulfinyl]-1H-thieno[3,4-d]imidazole 2-[4-(2,4-difluorophenoxy)-2-picolylsulfinyl]-1H-thieno-[3,4-d]imidazole 2-[4-(3-trifluoromethylphenoxy)-2-picolylsulfinyl]-1H-thieno[3,4-d]imidazole 2-[4-(4-fluorophenoxy)-2-picolylsulfinyl]-1H-thieno[3,4-d]imidazole 2-[4-(4-chlorophenoxy)-2-picolylsulfinyl]-1H-thieno[3,4-d]imidazole Alkyl and radicals derived therefrom such as, for example, alkoxy, alkylmercapto, alkylsulfinyl, alkylsulfonyl, aralkyl or alkanoyl can be straight-chain or branched.

($C_6$-$C_{12}$)-Aryl is, for example, phenyl, naphthyl or biphenylyl, phenyl being preferred.

($C_7$-$C_{11}$)-Aralkyl is, for example, benzyl or phenethyl, preferably benzyl. The same applies to radicals derived therefrom, such as aralkoxy.

Halogen stands for fluorine, chlorine, bromine or iodine.

Suitable $N^{im}$ protective groups $R^3$ are described, for example, in connection with substituted picolylsulfinylbenzimidazoles in EP-A-176,308 and EP-A2-221,041, and for thienoimidazole compounds in EP-A-234,485.

Preferred $N^{im}$ protective groups are those which can be cleaved in the presence of acids, preferably in a pH range from about 1–6 and/or under physiological conditions.

Optionally, chiral carbon and sulfur atoms which are present can exist both in the R and the S configuration. In such cases, the compounds of the formula I exist in the form of the pure enantiomers or as a mixture of stereoisomers (such as a mixture of enantiomers and a mixture of diastereomers).

Suitable salts are, in particular, alkali metal and alkaline earth metal salts, and salts with physiologically tolerable amines.

The invention furthermore relates to a process for the preparation of compounds of the formula I, which comprises a) reacting compounds of the formula II

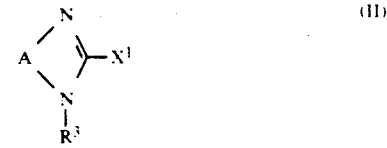

in which A, $R^1$, $R^2$ and $R^3$ are as defined above and $X^1$ denotes
  i. a leaving group or
  ii. —SH, —S⁻M⁺ or —SO$_2$—M⁺, with compounds of the formula III

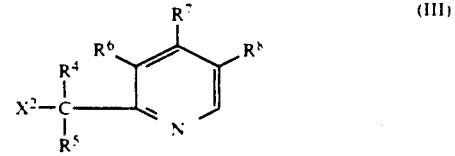

in which $R^4$, $R^5$, $R^6$, $R^7$ and $R^8$ are as defined above and $X^2$ in the abovementioned case denotes i. —SH, —S⁻M⁺ or —SO$_2$—M⁺ and in the abovementioned case ii. preferably denotes a leaving group or OH, or b) reacting compounds of the formula IV

in which A, $R^1$, $R^2$ and $R^3$ are as defined above, with compounds of the formula V

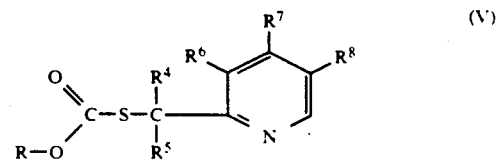

in which $R^4$, $R^5$, $R^6$, $R^7$ and $R^8$ are as defined above and R stands for an esterified group, i. in compounds of the formula I, oxidizing (an) optionally present —S— group(s), if desired, to give (an) —SO— or —SO$_2$— group(s).

ii. in compounds of the formula I, oxidizing (an) optionally present —SO— group(s), if desired, to give (an) —SO$_2$— group(s).

iii. if desired acylating, alkylating or aralkylating compounds of the formula I, in which R$^3$ stands for hydrogen.

iv. if desired hydrolyzing compounds of the formula I, wherein R$^3$ does not denote hydrogen, and v. converting compounds of the formula I, if desired, into their physiologically tolerable salts, where two or more of the measures i.–iv. can also be carried out in a sequence other than that indicated.

M$^+$ stands for cations such as, for example, ions of alkali metals or alkaline earth metals, or ammonium or alkylammonium ions, in particular sodium ions or potassium ions.

If, according to the process variant (a) preferred here, compounds of the formula II are reacted with compounds of the formula III, then X$^1$ or X$^2$ stands for a leaving group which can be removed nucleophilically, such as Cl, Br, I, —O—SO$_2$—CH$_3$, —O—SO$_2$—CF$_3$ or —O—SO$_2$—(C$_6$H$_4$—pCH$_3$).

The reaction of a compound of the formula II with a compound of the formula III or its salts takes place in an inert solvent such as, for example, water, methylene chloride, methanol, ethanol, acetone, ethyl acetate, toluene, tetrahydrofuran, acetonitrile, dimethylformamide, dimethyl sulfoxide or mixtures of these solvents, expediently in the presence of an inorganic or organic base, such as, for example, hydroxides, carbonates, alkoxides, hydrides or amides of sodium or potassium, ammonia, triethylamine, tributylamine or pyridine at −20° to +150° C., preferably at 0°–80° C.

The compounds of the formula II are known compounds (see, for example, Gronowitz, "The Chemistry of Heterocyclic Compounds", Band 44, "Thiophene and its Derivatives", Parts 1-3, New York 1985-6) or can be prepared in analogy to known processes, for example by ring closure of suitably substituted 2,3-, 3,4- or 4,5-diaminothiophenes of the formula IV defined above with suitable sulfur compounds such as carbon disulfide (for example DE-A-3,132,167).

The 2,3-, 3,4- or 4,5-diaminothiophenes necessary for this are either known from the literature or can be prepared in analogy to known processes. They are, for example, obtained by reduction of suitably substituted aminonitrothiophenes.

In the esters of the formula V employed in process variant (b), R stands for an esterified group, preferably (C$_1$–C$_6$)-alkyl or benzyl.

The reaction of a compound of the formula IV with a compound of the formula V according to process variant (b) takes place analogously to the procedures described in Preston et al., Benzimidazoles and Congeneric Tricyclic Compounds, Part 1, New York, pages 10–13.

The compounds of the formula I thus obtained can, if R$^3$ denotes hydrogen, be converted into physiologically tolerable salts.

Compounds of the formula I having T=—S— can furthermore be converted into those having T=—SO— or —SO$_2$— using suitable oxidants. In the same way, —S— groups in the substituents R$^1$, R$^2$ and R$^7$ can be oxidized.

This reaction takes place in a suitable, inert solvent such as, for example, methylene chloride, chloroform, carbon tetrachloride, 1,2-dichloroethane, toluene, ethyl acetate, acetic acid, trifluoroacetic acid, water, methanol, ethanol or mixtures thereof at −20° C. to −150° C., preferably at −10° C. to +40° C.

Suitable oxidants are, for example: hydrogen peroxide, peracids and peresters such as peracetic acid, trifluoroperacetic acid, monoperphthalic acid, m-chloroperbenzoic acid and its ester, ozone, dinitrogen tetroxide, iodobenzene, N-chlorosuccinimide, 1-chlorobenzotriazole, sodium hypochlorite, potassium peroxodisulfate, t-butyl hypochlorite, tetrabutylammonium periodate or permanganate, sodium metaperiodate, selenium dioxide or manganese dioxide, ceric ammonium nitrate, chromic acid, chlorine, bromine, diazabicyclo-[2.2.2]octane-bromine complex, dioxane dibromide, pyridinium perbromide, sulfuryl chloride, 2-arylsulfonyl-3-aryloxaziridines, titanium tetraisopropoxide/tert.-butyl hydroperoxide (optionally with the addition of dialkyl esters of (D)- or (L)-tartaric acid and a defined amount of water).

Likewise, isolated, optionally immobilized oxidizing enzymes or microorganisms can be used as oxidants.

The oxidants are employed in equimolar amounts, if appropriate even in a slight excess of 5–10 mole % in the oxidation to T=—SO— or even in a large excess and/or at a higher reaction temperature when oxidation to T=—SO$_2$— is desired.

The invention furthermore relates to new intermediates of the formula III. They can be prepared by methods known to the person skilled in the art, such as, for example, are described in "The Chemistry of Heterocyclic Compounds - Pyridine and its Derivatives", Pts. 2 and 3, E. Klingsberg Ed. Interscience Publishers, 1962.

In addition to the synthesis of the compounds of the formula III, where X$^2$ denotes a leaving group, from compounds of the formula III, in which X$^2$ denotes a hydroxyl group, the compounds of the formula III, in which X$^2$ denotes chlorine or bromine, can be prepared, for example, by halogenation of the corresponding 2-picolines with N-bromosuccinimide, trichloroisocyanuric acid (Chem. Ber. 120, 649-651 (1987)) or other N-haloamides such as N-chlorophthalimide.

Without limiting the invention to the following examples, several preparation processes for compounds of the formula III, in which X$^2$ denotes hydroxyl, are described below. Their conversion into compounds of the formula III, in which X$^2$ denotes a leaving group, takes place by standard methods.

Compounds of the formula III, in which X$^2$ denotes a hydroxyl group, R$^6$ and R$^8$ denote identical or different hydrogen or methyl, and R$^7$ denotes a monosubstituted or polysubstituted (C$_6$–C$_{12}$)-aryloxy or (C$_7$–C$_{11}$)-aralkoxy radical, are obtained from nitro compounds of the formula VI or chlorine compounds of the formula VII.

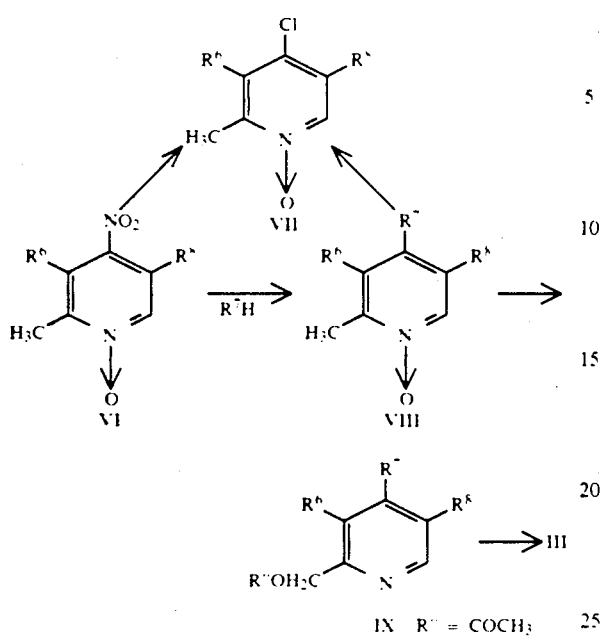

IX R" = COCH₃

A compound of the formula VI or VII is brought to reaction in an inert solvent such as, for example, tetrahydrofuran, dioxane, acetonitrile, acetone, methyl ethyl ketone, dimethyl sulfoxide, dimethylformamide, dimethylacetamide, hexamethylphosphoric triamide or 1,3-dimethyl-3,4,5,6-tetrahydro-2-(1H)-pyrimidinone, in the presence of an organic or inorganic base such as, for example, the hydroxide, hydrogen carbonate, carbonate, hydride or propoxide of sodium, lithium carbonate, the hydroxide, carbonate, hydride, hydrogen carbonate or tert.-butoxide of potassium, with an alcohol of the formula R⁷H between 0° C. and the boiling point of the solvent.

The preparation of the compounds of the formula III from compounds of the formula VII, which are prepared by the action of chlorinating agents such as, for example, acetyl chloride, thionyl chloride and phosphorus oxychloride on compounds of the formula VI, can be advantageous compared to the reaction with compounds of the formula VI.

4-Fluoro-2-picoline (J. Prakt. Chem. 9, 164-172 (1959)) and 4-fluoro-2-picoline-N-oxide, which is analogous to VII, can also be used.

Without limiting the invention to the examples mentioned below, 4-fluoro-, 4-chloro-, 4-trifluoromethyl-, 2,4-difluoro-, 3,5-difluoro-, 3,5-dichloro-, 3,5-bistrifluoromethyl- and pentafluorobenzyl alcohol, 4-fluoro-, 4-chloro-, 3-trifluoromethyl-, 2,4-difluorophenol and pentafluorophenol are employed, for example, as alcohols.

The compounds of the formula VIII thus obtained are reacted with trifluoroacetic anhydride at 0° C. or with acetic anhydride, if necessary in the presence of an acid, such as, for example, glacial acetic acid, at 80°-120° C. to give the acetates of the formula IX.

Their alkaline hydrolysis using hydroxides or carbonates of alkali metals in methanol, ethanol, water or similar solvents leads to the compounds of the formula III, in which X² denotes hydroxyl.

Compounds of the formula III, in which X² denotes a hydroxyl group, R⁶ denotes an alkoxy radical and R⁸ denotes hydrogen, can be prepared by the following process.

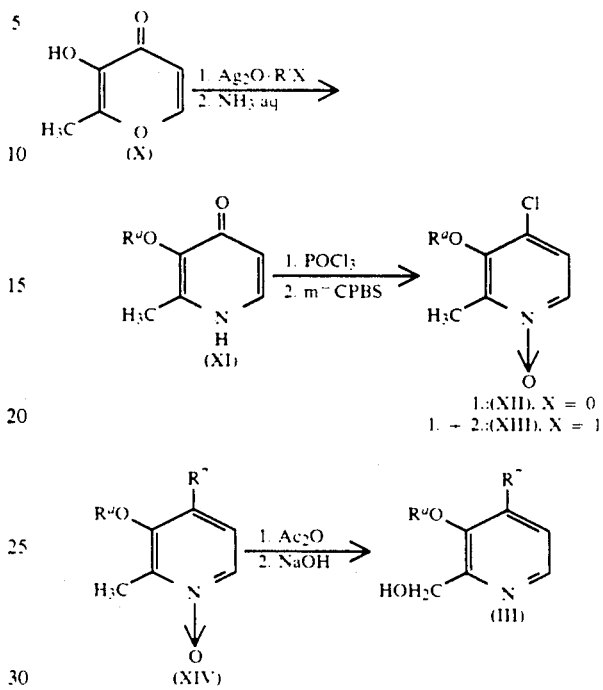

Maltol X reacts, for example, with a halide RᵃX in the presence of silver oxide or with fluoroalkyl triflates to give 3-alkoxypyran-4-ones which are reacted with aqueous ammonia to give 2-methyl-3-alkoxy-4-pyridones of the formula XI (J. Org. Chem. 29, 776 (1964)).

Using a halogenating agent, for example POCl₃, the compounds of the formula XI are converted into 2-methyl-3-alkoxy-4-chloropyridines, from which 4-alkoxy derivatives are obtained using an alcohol R⁷H in the presence of a base.

The reaction of the analogous N-oxides XIII with alcoholates to give compounds of the formula XIV is advantageous.

The substituted benzyl alcohols and phenols utilized have been mentioned previously.

Compounds of the formula XI can also be reacted directly to compounds of the formula XV in the presence of silver oxide.

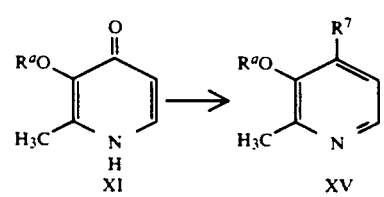

The invention furthermore relates to compounds of the formula III which can be obtained in an analogous manner by employing the isomeric 5-hydroxy-2-methyl-4-pyranone of the formula XVII, which, for example, is prepared from kojic acid XVI as described in J. Chem. Soc. 1956, 2558, instead of maltol X.

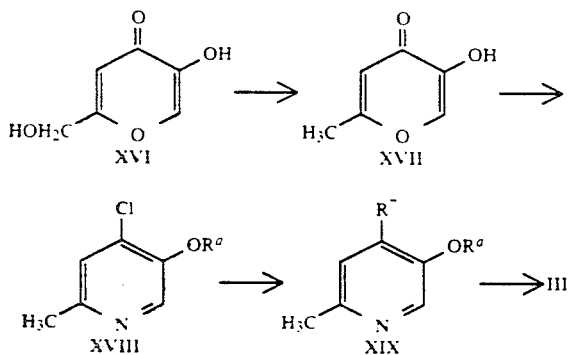

Processes for the preparation of 3,4-dialkoxy-2-picolines and 4,5-dialkoxy-2-picolines have also been described in EP-A-166,287 and EP-A-208,452.

The novel compounds of the formula I and their salts possess valuable pharmacological properties.

They clearly inhibit gastric acid secretion and, moreover, exhibit an excellent gastric and intestinal protective action.

"Gastric and intestinal protection" is taken in this connection to mean the prevention and treatment of gastrointestinal disorders, in particular inflammatory gastrointestinal disorders and lesions (such as, for example, gastric ulcer, duodenal ulcer, gastritis, or gastric irritation caused by hyperacidity or medicaments), which, for example, can be caused by microorganisms, bacterial toxins, medicaments (for example antiphlogistics and antirheumatics), chemicals (for example ethanol), gastric acid or stress situations.

On the basis of their excellent properties, the substituted thienoimidazoles of the formula I and their pharmacologically tolerable salts are outstandingly suitable for employment in human and veterinary medicine, where they can be used in particular for the treatment and prophylaxis of disorders of the stomach and intestine and those disorders which are based on excessive gastric acid secretion.

It has been found that the colon $H^+/K^+$ ATPase (compare Gustin and Goodman, J. Biol. Chem. 256 [1981]10651-10656) is strongly inhibited in vitro by compounds which are formed by treating the compounds of the formula I according to the invention with acid (for example with sodium acetate/HCl buffer having a pH of about 4-5.5). Such conversion products can also be formed in vivo by the passage of the compounds of the formula I through the gastrointestinal tract. To what extent they are formed depends on the substitution pattern and the pH.

A decisive influence on the electrolyte balance in the intestinal mucosa is attributed to the colon $H^+/K^+$ ATPase. Colon $H^+/K^+$ ATPase inhibitors, such as those mentioned above, can therefore intervene in this balance and be used for the treatment of disorders having a disturbed electrolyte balance.

The invention therefore also relates to the use of compounds of the formula I or their acid conversion products in the treatment of diarrheal illnesses. Examples of such disorders are inflammatory gastric illnesses, such as cholera, paratyphoid, travel diarrhea or other forms of secretory diarrhea, but also ulcerative colitis, Crohn's disease and regional enteritis.

The invention furthermore relates to conversion products which are formed by treating compounds of the formula I with acid.

The invention therefore further relates to the compounds of the formula I according to the invention for use in the treatment and prophylaxis of the previously mentioned disorders.

Likewise, the invention embraces the use of the compounds according to the invention in the preparation of medicaments which are employed for the treatment and prophylaxis of the previously mentioned disorders.

The invention further relates to medicaments which contain one or more compounds of the general formula I and/or their pharmacologically tolerable salts and also inclusion compounds of compounds of the formula I and cyclodextrin, preferably β-cyclodextrin.

The medicaments are prepared by processes which are known per se and which are familiar to the person skilled in the art. The pharmacologically active compounds according to the invention (=active compounds) are either employed as medicaments as such, or preferably in combination with suitable pharmaceutical auxiliaries in the form of tablets, dragees, capsules, suppositories, emulsions, suspensions or solutions, where the active compound content is advantageously between 0.1 and 96%.

Which auxiliaries are suitable for the desired medicament formulations are familiar to the person skilled in the art on the basis of his knowledge. In addition to solvents, gel-forming agents, suppository bases, tableting auxiliaries and other active compound excipients, antioxidants, dispersing agents, emulsifiers, defoaming agents, flavor-correcting agents, preservatives, solubilizing agents or colorants can, for example, be used.

The active compounds can be administered orally or parenterally, oral administration being preferred.

In general, it has proved advantageous in human medicine to administer the active compound(s) in oral doses in a daily dose of about 0.01 to about 20 mg/kg of body weight, if appropriate in the form of several, preferably 1 to 4, individual doses, to obtain the desired results. With parenteral administration, similar or (in particular in intravenous administration of the active compound), as a rule, lower dosages, can be used. The determination of the optimum dosage in each case and the type of administration of the active compound can easily take place by anyone skilled in the art on the basis of his expert knowledge.

If the compounds according to the invention and/or their salts are to be employed for the treatment of the above-mentioned disorders, then the pharmaceutical preparations can also contain one or more pharmacologically active constituents of other medicament groups, such as antibiotics, for example ofloxazine, antacids, for example aluminum hydroxide, magnesium aluminate, sucralfate, Bi salts, tranquillizers, such as benzodiazepines, for example diazepam; spasmolytics, such as, for example, bietamiverine, camylofine; anticholinergics, such as, for example, pirenzepine, telezepine, oxyphencyclimine, phencarbamide; local anesthetics, such as, for example; tetracaine, procaine; and optionally also gastrin antagonists, enzymes, vitamins or aminoacids. To give a form for oral use, the active compounds are mixed with the additives customary for this purpose, such as excipients, stabilizers or inert diluents, and brought into a suitable form for administration, such as tablets, dragees, hard gelatin capsules, aqueous, alcoholic or oily suspensions or aqueous, alcoholic or oily solutions, by customary methods. Gum arabic, magnesium oxide, magnesium carbonate, lactose, glucose or starch, in particular maize starch, can, for example, be used as inert excipients. In this case, the preparation can take place both as dry or moist granules. Possible oily excipients or solvents are, for example, vegetable and animal oils, such as sunflower oil or codliver oil.

For subcutaneous or intravenous administration, the active compounds or their physiologically tolerable salts are brought into solution, suspension or emulsion, if desired with the substances customary for this purpose, such as solubilizing agents, emulsifiers or further auxiliaries. Suitable solvents for the novel active compounds and the corresponding physiologically tolerable salts are, for example: water, physiological saline solutions or alcohols, for example ethanol, propanol or glycerol, in addition to sugar solutions such as glucose or mannitol solutions, and also a mixture of the different solvents mentioned.

The following examples serve to illustrate the procedures according to the invention, without limiting the invention to the representative substances mentioned here.

The melting and decomposition points indicated are not corrected or standardized.

EXAMPLE 1

4-Chloro-2-picoline-N-oxide 15.4 g (0.1 mol) of 4-nitro-2-picoline-N-oxide are added in portions at 0° C. to 75 ml of acetyl chloride. On warming to room temperature, a clear solution results which is added dropwise to ice with stirring. After adding $K_2CO_3$, the mixture is extracted several times using dichloromethane and ethyl acetate. After evaporating, the product is purified chromatographically on silica gel. The oil obtained crystallizes on standing, m.p. 37° C.

EXAMPLE 2

4-(4-Trifluoromethylbenzyloxy)-2-picoline-N-oxide 11.2 g (100 mmol) of potassium tert.-butoxide are added under an $N_2$ atmosphere at 25° C. to 25 ml (183 mmol) of 4-trifluoromethylbenzyl alcohol. 7.2 g (50 mmol) of 4-chloro-2-picoline-N-oxide are subsequently added dropwise, then 10 ml of tert.-butanol are added, and the mixture is stirred for 1 hour at 25° C. and for 30 minutes at 75°–80° C. Water is then added and the mixture is extracted three times using dichloromethane, the extracts are dried and concentrated, and the residue is chromatographed on silica gel using dichloromethane/methanol. The product is obtained from the corresponding fractions, m.p. 113°–115° C.

EXAMPLE 3

4-(4-Trifluoromethylbenzyloxy)-2-hydroxymethylpyridine 3.4 g (12 mmol) of the title compound from Example 2 are warmed to 80° C. in 5 ml of glacial acetic acid and 10 ml of acetic anhydride are added dropwise at this temperature with stirring. The mixture is then warmed to 110°–120° C. for 2 hours, allowed to cool to 80° C., 10 ml of methanol are added, the mixture is heated to reflux for a further 15 minutes and subsequently concentrated. The residue is taken up in 10 ml of methanol and rapidly added dropwise at 10° C. to 50 ml of 2N methanolic NaOH. The solution is then clarified over charcoal, concentrated, the residue treated with 50 ml, extracted three times using 50 ml of dichloromethane, and the organic phase dried and concentrated. The crystallized residue is triturated with a petroleum ether/diisopropyl ether mixture (1:1), and the product is filtered off with suction, washed with a little diisopropyl ether and dried in vacuo, m.p. 96°–98° C.

EXAMPLE 4

4-(4-Trifluoromethylbenzyloxy)-2-chloromethylpyridine 2.2 g (7.8 mmol) of the title compound from Example 3 are dissolved in 50 ml of anhydrous dichloromethane and a solution of 2 ml of thionyl chloride in 6 ml of dichloromethane is added dropwise at −10° C. The mixture is warmed to room temperature, stirred for 30 minutes more, and concentrated. The crystalline residue is brought to crystallization using diisopropyl ether and dried using an oilpump, m.p. 133°–135° C.

EXAMPLE 5

2-[4-(4-Trifluoromethylbenzyloxy)-2-picolylmercapto]-1H-thieno[3,4-d]imidazole dihydrochloride 0.625 g (4 mmol) of 2-mercaptothieno[3,4-d]imidazole are added at 25° C. to 1.35 g (4 mmol) of the title compound from Example 4 in 50 ml of ethanol, and the mixture is stirred at 60° C. for 1.5 hours. The reaction mixture is concentrated in vacuo, and the residue is treated with acetone, filtered off with suction, washed with acetone and dried in vacuo, m.p. 180°–182° C.

EXAMPLE 6

2-[4-(4-Trifluoromethylbenzyloxy)-2-picolylmercapto]-1H-thieno[3,4-d]imidazole 1.5 g (3.0 mmol) of the dihydrochloride from Example 5 are suspended in 25 ml of methanol with ice-cooling and under a nitrogen atmosphere and 1.7 ml (about 12 mmol) of triethylamine are added dropwise, by means of which a clear solution is formed which is subsequently clarified over activated charcoal and concentrated. On treating with water, the residue crystallizes and is washed with water and dried in vacuo, m.p. 141°–143° C. with decomposition.

EXAMPLE 7

2-[4-(4-Trifluoromethylbenzyloxy)-2-picolylsulfinyl]-1H-thieno[3,4-d]imidazole

A solution of 0.5 g (2.5 mmol, 85%) of m-chloroperbenzoic acid in 10 ml of dichloromethane is added dropwise with stirring at 0° to 5° C. to 1.0 g (2.37 mmol) of the title compound from Example 6 in a two-phase mixture of 200 ml of dichloromethane and 100 ml of aqueous $KH_2PO_4/Na_2HPO_4$ buffer solution (pH=7.5). The organic phase is separated off, shaken with saturated aqueous $NaHCO_3$ solution, dried over $MgSO_4$, clarified over activated charcoal and concentrated. The crystalline evaporation residue is treated with ethyl acetate, filtered off with suction and washed twice with a little ethyl acetate. The colorless crystalline product is dried in vacuo, m.p. 149° C. with decomposition.

EXAMPLE 8

4-(2,4-Difluorophenoxy)-2-picoline-N-oxide 4.3 g (30 mmol) of 4-chloro-2-picoline-N-oxide are added to a mixture of 4.6 g (35 mmol) of 2,4-difluorophenol in 25 ml of N,N-dimethylacetamide and 4.9 g (35 mmol) of finely powdered potassium carbonate and the mixture is warmed to 140° C. for 3 hours with stirring. After cooling, the reaction mixture is poured into 250 ml of water, extracted three times using dichloromethane, and the organic phases are dried over MgSO₄ and concentrated. The residue is taken up in dichloromethane and extracted by shaking with saturated aqueous NaCl solution. After drying and freeing from solvent, the extract is brought to crystallization using diisopropyl ether and washed with ethyl acetate. Colorless crystals, m.p. 112°–124° C.

The following Examples 9 to 72 were prepared analogously to Examples 1 to 8 and to the synthesis schemes shown:

| Example No. | Y | R⁶ | R⁹ | R¹⁰ | R¹¹ | R¹² | R¹³ | m.p. [°C] |
|---|---|---|---|---|---|---|---|---|
| 9 | 1 | H | H | H | F | H | H | 155–157 |
| 10 | 1 | H | H | CF₃ | H | CF₃ | H | 162–164 |
| 11 | 1 | H | F | H | F | H | H | 145–148 |
| 12 | 1 | H | H | F | H | F | H | * |
| 13 | 1 | H | H | F | F | H | H | 170–172 |
| 14 | 1 | H | H | H | Cl | H | H | 153–155 |
| 15 | 1 | H | H | Cl | H | Cl | H | 163–165 |
| 16 | 1 | OCH₃ | H | H | F | H | H | 78–80 |
| 17 | 1 | OCH₃ | H | H | CF₃ | H | H | 146–148 |
| 18 | 1 | OCH₃ | H | CF₃ | H | CF₃ | H | 164–167 |
| 19 | 1 | OCH₃ | H | F | F | H | H | * |
| 20 | 0 | H | H | CF₃ | H | H | H | oil* |

*without purifying, reacted further

| Example No. | Y | R⁶ | R⁹ | R¹⁰ | R¹¹ | R¹² | R¹³ | m.p. [°C] |
|---|---|---|---|---|---|---|---|---|
| 21 | 1 | H | H | H | F | H | H | 74–76 |
| 22 | 1 | H | H | CF₃ | H | CF₃ | H | 113–115 |
| 23 | 1 | H | F | H | F | H | H | 56–60 |
| 24 | 1 | H | H | F | H | F | H | oil* |
| 25 | 1 | H | H | F | F | H | H | oil* |
| 26 | 1 | H | H | H | Cl | H | H | 79–82 |
| 27 | 1 | H | H | Cl | H | Cl | H | 114–115 |
| 28 | 1 | OCH₃ | H | H | F | H | H | 106–107 |
| 29 | 1 | OCH₃ | H | H | CF₃ | H | H | 100–101 |
| 30 | 1 | OCH₃ | H | CF₃ | H | CF₃ | H | 88–90 |
| 31 | 1 | OCH₃ | H | F | F | H | H | 93–95 |
| 32 | 0 | H | H | CF₃ | H | H | H | oil* |
| 33 | 0 | H | F | H | F | H | H | 62–64 |

*reacted further

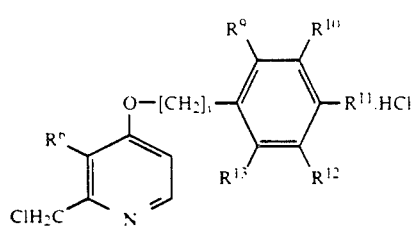

| Example No. | Y | R⁶ | R⁹ | R¹⁰ | R¹¹ | R¹² | R¹³ | m.p. [°C] |
|---|---|---|---|---|---|---|---|---|
| 34 | 1 | H | H | H | F | H | H | 142–143 |
| 35 | 1 | H | H | CF₃ | H | CF₃ | H | 167–169 |
| 36 | 1 | H | F | H | F | H | H | 143–144 |
| 37 | 1 | H | H | F | H | F | H | hygroscopic* |
| 38 | 1 | H | H | F | F | H | H | 136–138 |
| 39 | 1 | H | H | H | Cl | H | H | 154–156 |
| 40 | 1 | H | H | Cl | H | Cl | H | 159–160 |
| 41 | 1 | OCH₃ | H | H | F | H | H | 133–135 |
| 42 | 1 | OCH₃ | H | H | CF₃ | H | H | 155–156 |
| 43 | 1 | OCH₃ | H | CF₃ | H | CF₃ | H | 151–152 |
| 44 | 1 | OCH₃ | H | F | F | H | H | hygroscopic* |
| 45 | 0 | H | H | CF₃ | H | H | H | resin* |
| 46 | 0 | H | F | H | F | H | H | 97–100 |

*reacted further

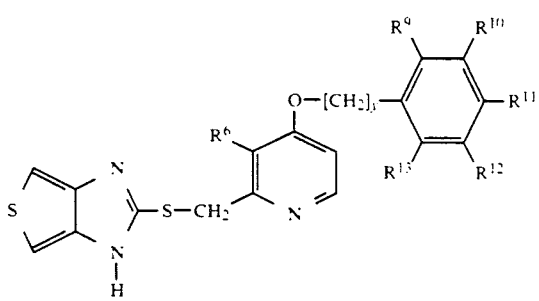

| Example No. | Y | R⁶ | R⁹ | R¹⁰ | R¹¹ | R¹² | R¹³ | m.p. [°C] |
|---|---|---|---|---|---|---|---|---|
| 47 | 1 | H | H | H | F | H | H | 141 |
| 48 | 1 | H | H | CF₃ | H | CF₃ | H | 187 |
| 49 | 1 | H | F | H | F | H | H | 160–161 |
| 50 | 1 | H | H | F | H | F | H | 142–143 |
| 51 | 1 | H | H | F | F | H | H | 143–145 |
| 52 | 1 | H | H | H | Cl | H | H | 156–158 |
| 53 | 1 | H | H | Cl | H | Cl | H | 178–179 |
| 54 | 1 | OCH₃ | H | H | F | H | H | 147–149 |
| 55 | 1 | OCH₃ | H | H | CF₃ | H | H | 138–139 |
| 56 | 1 | OCH₃ | H | CF₃ | H | CF₃ | H | 135–137 |
| 57 | 1 | OCH₃ | H | F | F | H | H | 150 |
| 58 | 0 | H | H | CF₃ | H | H | H | 154–155 |
| 59 | 0 | H | F | H | F | H | H | 129–131 |

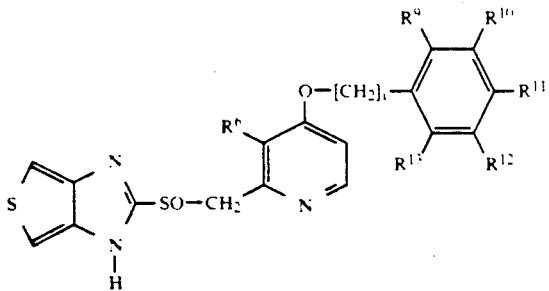

| Example No. | Y | R^r | R^q | R^10 | R^11 | R^12 | R^13 | m.p. [°C.] and dec |
|---|---|---|---|---|---|---|---|---|
| 60 | 1 | H | H | H | F | H | H | 145 |
| 61 | 1 | H | H | CF₃ | H | CF₃ | H | 135–136 |
| 62 | 1 | H | F | H | F | H | H | 117–118 |
| 63 | 1 | H | H | F | H | F | H | 159–161 |
| 64 | 1 | H | H | F | F | H | H | 151 |
| 65 | 1 | H | H | H | Cl | H | H | 144–145 |
| 66 | 1 | H | H | Cl | H | Cl | H | 102–104 |
| 67 | 1 | OCH₃ | H | H | F | H | H | 119–121 |
| 68 | 1 | OCH₃ | H | H | CF₃ | H | H | 148–149 |
| 69 | 1 | OCH₃ | H | CF₃ | H | CF₃ | H | 157–158 |
| 70 | 1 | OCH₃ | H | F | F | H | H | 120 |
| 71 | 0 | H | H | CF₃ | H | H | H | 119–121 |
| 72 | 0 | H | F | H | F | H | H | 122–124 |

If not described explicitly, the following Examples are obtained analogously to Examples 2–8:

EXAMPLE 73

4-(4-Fluorophenoxy)-2-picoline-N-oxide 6.2 g (55 mmol) of 4-fluorophenol are dissolved in 75 ml of N,N-dimethylacetamide and 20.7 g (150 mmol) of finely powdered potassium carbonate was added. 7.7 g (50 mmol) of 4-nitro-2-picoline-N-oxide are added to this suspension and the mixture is warmed at 80° C. for 3 hours. A further 7 g (50 mmol) of potassium carbonate are subsequently added and the mixture is stirred for one hour at 100° C. After cooling, it is freed from N,N-dimethylacetamide in vacuo, and the residue is taken up in water, extracted a number of times using dichloromethane, dried over MgSO₄ and concentrated, and the residue is brought to crystallization using diisopropyl ether, m.p. 122°–124° C.

EXAMPLE 74

4-(4-Fluorophenoxy)-2-hydroxy-methylpyridine, m.p. 75°–77° C. (from diisopropyl ether)

EXAMPLE 75

4-(4-Fluorophenoxy)-2-chloromethylpyridine hydrochloride, oily crude product, reacted further in Example 76.

EXAMPLE 76

2-[4-(4-Fluorophenoxy)-2-picolylmercapto]-14-thieno[3,4-d]imidazole 1.60 g (10 mmol) of 2-mercaptothieno[3,4-d]imidazole are suspended in 100 ml of methanol and 7 ml of 5.5M sodium methoxide solution are added. A solution of 3.0 g (10 mmol) of the title compound from Example 75 in 20 ml of methanol is added dropwise to the resulting clear solution at room temperature and the mixture is heated under reflux for 1 hour. The solution is concentrated, water is added to the residue and the mixture is extracted with dichloromethane. The organic phase is dried over MgSO₄ and concentrated, and the residue is brought to crystallization using diethyl ether. The pale brown crude product is recrystallized from ethyl acetate/active carbon. m.p. 157°–159° C.

EXAMPLE 77

2-[4-(4-Fluorophenoxy)-2-picolylsulfinyl]-1H-thieno[3,4-d]imidazole. m.p. 146° C. [dec.] (from ethyl acetate).

EXAMPLE 78

4-(4-Chlorophenoxy)-2-picoline-N-oxide, m.p. 81°–83° C. (from diisopropyl ether), preparation analogous to Example 73.

EXAMPLE 79

4-(4-Chlorophenoxy)-2-hydroxymethyl-pyridine, m.p. 64°–65° C. (from diisopropyl ether)

EXAMPLE 80

4-(4-Chlorophenoxy)-2-chloromethyl-pyridine hydrochloride, m.p. 156°–157° C. (from ethyl acetate)

EXAMPLE 81

2-[4-(4-Chlorophenoxy)-2-picolyl-mercapto]-1H-thieno[3,4-d]imidazole, m.p. 150°–151° C. [dec.] (from ethyl acetate/diethyl ether)

EXAMPLE 82

2-[4-(4-Chlorophenoxy)-2-picolyl-sulfinyl]-1H-thieno[3,4-d]imidazole, m.p. 140°–141° C. [dec.] (from ethyl acetate)

EXAMPLE 83

4-(3,5-Bistrifluoromethylphenoxy)-2-picoline-N-oxide a) 1.84 g (16.5 mmol) of potassium tert. butoxide are introduced in portions at 20° C. with vigorous stirring and under a nitrogen atmosphere into 3.45 g (15 mmol) of 3,5-bistrifluoromethylphenol, dissolved in 10 ml of tert. butanol. Tert. butanol is subsequently distilled off, the residue is taken up in 10 ml of N,N-dimethylacetamide and 1.66 g (15 mmol) of 4-fluoro-2-picoline in 2 ml of N,N-dimethylacetamide are added dropwise at 20° C. The reaction mixture is then heated at 135°–140° C. for 4 hours, water is added and the mixture is extracted using dichloromethane. The oily crude product is chromatographed using ethyl acetate/toluene (5:1) on silica gel. ($R_f = 0.4$).

b) 4.3 g (13.3 mmol) of the product from Ex. 83 a) are oxidized in dichloromethane at 20° C. with stirring using 2.7 g (13.3 mmol) of 85% strength m-chloroperbenzoic acid. The organic phase is extracted by shaking with saturated aqueous NaHCO₃ solution after 2 hours, dried and concentrated, oily product, $R_f$(ethyl acetate/methanol = 8:1) = 0.08.

EXAMPLE 84

4-(3,4-Dichlorophenoxy)-2-picoline-N-oxide, m.p. 125°–127° C. (from petroleum ether), preparation analogous to Example 73

EXAMPLE 85

4-(3,4-Dichlorophenoxy)-2-hydroxymethyl-pyridine, m.p. 103°–105° C. (from diisopropyl ether)

EXAMPLE 86

4-(3,4-Dichlorophenoxy)-2-chloromethylpyridine hydrochloride. m.p. 173°–175° C. (from diisopropyl ether)

EXAMPLE 87

2-[4-(3,4-Dichlorophenoxy)-2-picolylmercapto]-1H-thieno[3,4-d]imidazole. m.p. 161°–163° C. (from ethyl acetate)

EXAMPLE 88

2-[4-(3,4-Dichlorophenoxy)-2-picolylsulfinyl]-1H-thieno-[3,4-d]imidazole. m.p. 116° C. (dec.; from toluene)

The following compounds of the formula

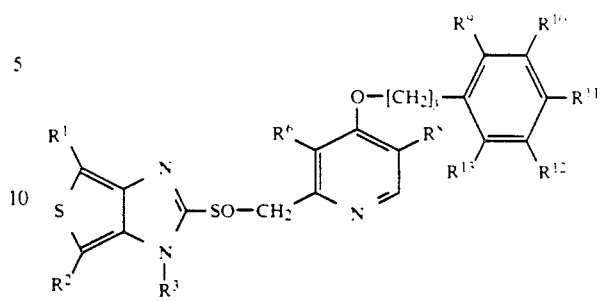

can be prepared in an analogous manner:

| | | | | | | | | | | |
|---|---|---|---|---|---|---|---|---|---|---|
| | | | $y = 1$; | | | | | | | |
| $R^1$ | $R^2$ | $R^3$ | $R^6$ | $R^8$ | $R^9$ | $R^{10}$ | $R^{11}$ | $R^{12}$ | $R^{13}$ | |
| H | H | H | H | H | F | F | F | F | F | |
| H | H | H | H | H | H | NO$_2$ | H | H | H | |
| H | H | H | H | H | Cl | H | CF$_3$ | H | H | |
| H | H | H | H | H | H | H | CN | H | H | |
| H | H | H | H | H | H | Cl | Cl | H | H | |
| H | H | H | CH$_3$ | H | H | H | CF$_3$ | H | H | |
| H | H | H | CH$_3$ | H | H | H | Cl | H | H | |
| H | H | H | CH$_3$ | H | H | Cl | H | Cl | H | |
| H | H | H | CH$_3$ | H | H | H | F | H | H | |
| H | H | H | CH$_3$ | H | H | Cl | Cl | H | H | |
| H | H | H | H | CH$_3$ | H | H | CF$_3$ | H | H | |
| H | H | H | H | CH$_3$ | H | Cl | H | Cl | H | |
| H | H | H | H | CH$_3$ | H | H | F | H | H | |
| H | H | H | H | CH$_3$ | H | H | Cl | H | H | |
| CH$_3$ | CH$_3$ | H | H | H | H | H | CF$_3$ | H | H | |
| CH$_3$ | CH$_3$ | H | H | H | H | H | F | H | H | |
| CH$_3$ | CH$_3$ | H | H | H | H | H | Cl | H | H | |
| CH$_3$ | CH$_3$ | H | H | H | H | Cl | H | Cl | H | |
| CH$_3$ | CH$_3$ | H | H | H | H | Cl | Cl | H | H | |
| CH$_3$ | CH$_3$ | H | CH$_3$ | H | H | H | CF$_3$ | H | H | |
| CH$_3$ | CH$_3$ | H | CH$_3$ | H | H | H | F | H | H | |
| CH$_3$ | CH$_3$ | H | CH$_3$ | H | H | Cl | Cl | H | H | |
| H | H | CH$_2$OAc | H | H | H | H | CF$_3$ | H | H | |
| H | H | (CH$_3$)CHOAc | H | H | H | H | CF$_3$ | H | H | |
| H | H | CH$_2$OAc | H | H | H | H | F | H | H | |
| H | H | CH$_2$OAc | CH$_3$ | H | H | H | F | H | H | |
| H | H | CH$_2$OAc | H | H | H | H | Cl | H | H | |
| H | H | CH$_2$OCOOEt | H | H | H | Cl | Cl | H | H | |
| H | H | CH$_2$OCOOEt | H | H | H | H | CF$_3$ | H | H | |
| H | H | CH$_2$OCOOEt | H | H | H | H | F | H | H | |
| OCH$_2$CF$_3$ | H | H | H | H | H | H | CF$_3$ | H | H | |
| OCH$_2$CF$_3$ | H | H | H | H | H | H | F | H | H | |
| OCH$_2$CF$_3$ | H | H | H | H | H | H | Cl | H | H | |
| OCH$_2$CF$_3$ | H | H | H | H | H | Cl | Cl | H | H | |
| OCH$_2$CF$_3$ | H | H | CH$_3$ | H | H | H | CF$_3$ | H | H | |
| OCH$_2$CF$_3$ | H | H | CH$_3$ | H | H | H | F | H | H | |
| OCH$_2$CF$_3$ | H | H | CH$_3$ | H | H | H | Cl | H | H | |
| OCH$_2$CF$_3$ | OCH$_2$CF$_3$ | H | H | H | H | H | CF$_3$ | H | H | |
| OCH$_2$CF$_3$ | OCH$_2$CF$_3$ | H | H | H | H | H | F | H | H | |
| OCH$_2$CF$_3$ | OCH$_2$CF$_3$ | H | H | H | H | H | Cl | H | H | |
| OCH$_2$CF$_2$CF$_3$ | H | H | CH$_3$ | H | H | H | CF$_3$ | H | H | |
| OCH$_2$CF$_2$CF$_3$ | H | H | CH$_3$ | H | H | H | F | H | H | |
| OCH$_2$CF$_2$CF$_3$ | H | H | CH$_3$ | H | H | H | Cl | H | H | |
| OCH$_2$CF$_2$CF$_3$ | OCH$_2$CF$_2$CF$_3$ | H | H | H | H | H | CF$_3$ | H | H | |
| OCH$_2$CF$_2$CF$_3$ | OCH$_3$ | H | H | H | H | H | F | H | H | |
| OCH$_2$CF$_2$CF$_3$ | OCH$_3$ | H | H | H | H | Cl | Cl | H | H | |
| OCH$_2$CF$_3$ | OCH$_3$ | H | H | H | H | Cl | Cl | H | H | |
| OCH$_2$CF$_3$ | OCH$_3$ | H | H | H | H | H | CF$_3$ | H | H | |
| OCF$_2$CF$_2$H | H | H | H | H | H | H | CF$_3$ | H | H | |
| OCF$_2$CF$_2$H | H | H | H | H | H | H | F | H | H | |
| OCF$_2$CF$_2$H | H | H | H | H | H | H | Cl | H | H | |
| OCF$_2$CF$_2$H | H | H | CH$_3$ | H | H | H | CF$_3$ | H | H | |
| OCF$_2$CF$_2$F | H | H | CH$_3$ | H | H | H | Cl | H | H | |
| OCF$_2$CF$_2$F | H | H | CH$_3$ | H | H | H | F | H | H | |
| H | H | CH$_2$OCOPh | H | H | H | H | CF$_3$ | H | H | |
| H | H | CH$_2$OCOOBz | H | H | H | H | CF$_3$ | H | H | |
| H | H | CH$_2$OCOOBz | H | H | H | H | F | H | H | |
| H | H | CH$_2$OAc | CH$_3$ | H | H | H | CF$_3$ | H | H | |

| R1 | R2 | R3 | R4 | R5 | R9 | R10 | R11 | R12 | R13 |
|---|---|---|---|---|---|---|---|---|---|
| H | H | H | H | H | F | F | F | F | F |
| H | H | H | CH3 | H | F | F | F | F | F |
| H | H | H | CH3 | CH3 | F | F | F | F | F |
| H | H | H | H | CH3 | F | F | F | F | F |
| CH3 | CH3 | H | H | H | F | F | F | F | F |
| CH3 | CH3 | H | CH3 | H | F | F | F | F | F |
| CH3 | CH3 | H | CH3 | CH3 | F | F | F | F | F |
| CH3 | CH3 | H | H | H | H | CF3 | H | H | H |
| CH3 | CH3 | H | CH3 | H | H | CF3 | H | H | H |
| CH3 | CH3 | H | H | CH3 | H | CF3 | H | H | H |
| H | H | H | CH3 | H | F | H | F | H | H |
| H | H | H | H | CH3 | F | H | F | H | H |
| H | H | H | H | H | H | CF3 | H | CF3 | H |
| H | H | H | CH3 | H | H | CF3 | H | CF3 | H |
| CH3 | CH3 | H | H | H | H | CF3 | H | CF3 | H |
| H | H | H | OCH3 | H | H | CF3 | H | H | H |
| CH3 | CH3 | H | OCH3 | H | H | CF3 | H | H | H |
| H | H | H | H | OCH3 | H | CF3 | H | H | H |
| CH3 | CH3 | H | OCH3 | H | F | H | F | H | H |
| H | H | H | OCH3 | H | H | CF3 | H | CF3 | H |
| H | H | H | OCH3 | H | F | H | F | H | H |
| H | H | H | H | H | Cl | H | Cl | Cl | H |
| H | H | H | CH3 | H | Cl | H | Cl | Cl | H |
| H | H | H | H | CH3 | Cl | H | Cl | Cl | H |
| H | H | H | OCH3 | H | Cl | H | Cl | Cl | H |
| CH3 | CH3 | H | H | H | Cl | H | Cl | Cl | H |
| H | H | H | H | H | F | H | F | F | H |
| H | H | H | H | H | H | Cl | H | Cl | H |
| H | H | H | OCH3 | H | H | Cl | H | Cl | H |
| CH3 | CH3 | H | H | H | H | Cl | H | Cl | H |
| H | H | H | H | OCH2CF3 | H | H | F | H | H |
| H | H | H | H | OCH2CF3 | H | F | H | F | H |
| H | H | H | H | OCH2CF3 | H | CF3 | H | H | H |
| H | H | H | H | OCH2CF3 | F | H | F | H | H |
| H | H | H | H | OCF2CF2H | F | H | F | H | H |
| H | H | H | H | OCF2CF2H | H | CF3 | H | H | H |
| H | H | H | OCH3 | H | H | H | F | H | H |
| CH3 | CH3 | H | OCH3 | H | H | H | F | H | H |
| H | H | H | OCHF2 | H | H | H | F | H | H |
| H | H | H | H | H | H | H | CF3 | H | H |
| H | H | H | CH3 | H | H | CF3 | H | CF3 | H |
| CH3 | CH3 | H | CH3 | H | H | CF3 | H | CF3 | H |
| CH3 | CH3 | H | H | H | H | H | CF3 | H | H |
| H | H | H | OCH3 | H | H | H | F | H | H |
| CH3 | CH3 | H | H | H | H | H | F | H | H |
| CH3 | CH3 | H | H | H | H | Cl | Cl | H | H |
| H | H | H | CH3 | H | H | H | Cl | H | H |
| CH3 | CH3 | H | H | H | H | H | Cl | H | H |
| H | H | H | CH3 | H | H | H | Cl | H | H |
| H | H | H | CH3 | H | H | H | F | H | H |
| H | H | H | CH3 | H | H | H | CF3 | H | H |
| CH3 | CH3 | H | H | H | H | H | CF3 | H | H |

What is claimed:

1. A compound of the formula I

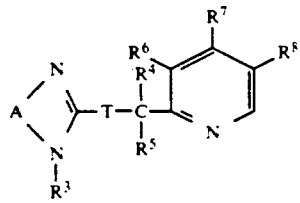

in which
A stands for

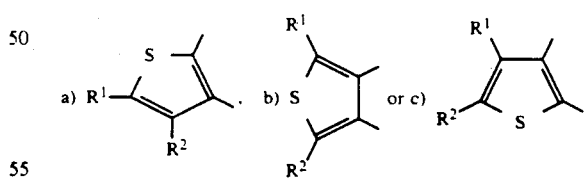

T denotes —S—, —SO— or —SO2, $R^1$ and $R^2$ are identical or different and denote hydrogen, $(C_1-C_3)$-alkyl, halogen, $(C_1-C_4)$-alkoxy, —O—$[CH_2-]_x C_f H_{(2f+1-g)} F_g$, or $(C_1-C_4)$-alkoxycarbonyl, $R^3$ denotes hydrogen, $(C_1-C_6)$-alkanoyl, $(C_1-C_6)$-alkylcarbamoyl, $(C_1-C_6)$-alkoxycarbonyl, benzyloxycarbonyl or another physiologically tolerable $N^{im}$ protecting group which can be cleaved in acidic medium and/or under physiological conditions selected from the group consisting of $(C_1-C_{10})$-acyloxy-$(C_1-C_6)$-alkyl, $(C_1-C_{10})$- alkanoyloxy-($C_1$-$C_6$)-alkyl, benzoyloxy-($C_1$-$C_6$)-alkyl, benzyloxycarbonyloxy-($C_1$-$C_6$)-alkyl or ($C_1$-$C_6$)-alkoxycarbonyloxy-($C_1$-$C_6$)-alkyl, $R^4$ and $R^5$ each denote hydrogen, $R^6$ and $R^8$ are identical or different and denote hydrogen, halogen, ($C_1$-$C_3$)-alkyl, ($C_1$-$C_6$)-alkoxy or a fluoroalkoxy radical of the formula —O—[$CH_2$—]$_x$$C_fH_{(2f+1-g)}$$F_g$, $R^7$ denotes a monosubstituted or polysubstituted benzyl-oxy or phenoxy radical of the formula

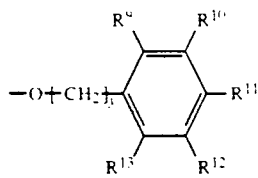

y is 0 or 1, $R^9$, $R^{10}$, $R^{11}$, $R^{12}$ and $R^{13}$ are identical or different and denote hydrogen, fluorine, chlorine, bromine, or trifluoromethyl, cyano, nitro, ($C_1$-$C_6$)-alkoxycarbonyl f is 1, 2, 3, 4, 5, 6, 7 or 8, g is 0, 1 to (2f+1), x is 0, 1, 2 or 3, or a physiologically tolerable salt thereof.

2. A compound of the formula I as claimed in claim 1, in which A is substituted as in claim 5 under b), or the physiologically tolerable salt thereof.

3. A compound of the formula I as claimed in claim 1, in which T stands for an —SO— group, or the physiologically tolerable salt thereof.

4. A compound of the formula I as claimed in claim 1, in which $R^1$ and $R^2$ are identical or different and denote hydrogen or ($C_1$-$C_3$)-alkyl $R^3$ is unchanged, $R^4$ and $R^5$ each denote hydrogen, $R^6$ and $R^8$ are identical or different and denote hydrogen, ($C_1$-$C_3$)-alkyl or ($C_1$-$C_3$)-alkoxy, $R^7$ denotes a monosubstituted or polysubstituted benzyloxy or phenoxy radical, $R^9$, $R^{10}$, $R^{11}$, $R^{12}$ and $R^{13}$ are identical or different and denote hydrogen, fluorine, chlorine, trifluoromethyl and the remaining radicals and variables are as defined in claim 1 or a physiologically tolerable salt thereof.

5. A compound of the formula I

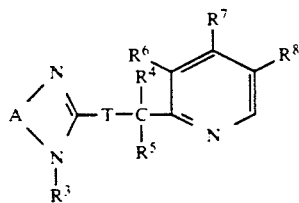

in which
A stands for

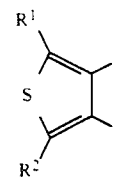

T denotes —S—, —SO— or —$SO_2$—, $R^1$ and $R^2$ are identical or different and denote hydrogen, halogen, cyano, nitro, trifluoromethyl, ($C_1$-$C_6$)-alkyl, ($C_1$-$C_6$)-hydroxyalkyl, ($C_1$-$C_6$)-alkoxy, —O—[$CH_2$—]$_x$$C_fH_{(2f+1-g)}$$F_g$, —$OCF_2Cl$, —O—$CF_2$—CHFCl, ($C_1$-$C_6$)-alkylmercapto, ($C_1$-$C_6$)-alkylsulfinyl, ($C_1$-$C_6$)-alkylsulfonyl, ($C_1$-$C_6$)-alkylcarbonyl, ($C_1$-$C_6$)-alkoxycarbonyl, carbamoyl, N-($C_1$-$C_4$)-alkylcarbamoyl, N,N-di-($C_1$-$C_4$)-alkylcarbamoyl, ($C_1$-$C_6$)-alkylcarbonyloxy, ($C_3$-$C_8$)-cycloalkyl, phenyl, benzyl, phenoxy, benzyloxy, anilino, N-methylanilino, phenylmercapto, phenylsulfonyl, phenylsulfinyl, sulfamoyl, N-($C_1$-$C_4$)-alkylsulfamoyl or N,N-di-($C_1$-$C_4$)-alkylsulfamoyl, $R^3$ denotes hydrogen, ($C_1$-$C_6$)-alkanoyl, ($C_1$-$C_6$)-alkylcarbamoyl, ($C_1$-$C_6$)-alkoxycarbonyl, benzyloxycarbonyl or another physiologically tolerable $N^{im}$ protecting group which can be cleaved in acidic medium and/or under physiological conditions, said physiologically tolerable $N^{im}$ protecting group is ($C_1$-$C_{10}$)-acyloxy-($C_1$-$C_6$)-alkyl, benzoyloxy-($C_1$-$C_6$)-alkyl, benzyloxycarbonyloxy-($C_1$-$C_6$)-alkyl or ($C_1$-$C_6$)-alkoxycarbonyloxy-($C_1$-$C_6$)-alkyl, $R^4$ and $R^5$ are identical or different and denote hydrogen or ($C_1$-$C_3$)-alkyl, $R^5$ and $R^8$ are identical or different and denote hydrogen, halogen, trifluoromethyl, ($C_1$-$C_{12}$)-alkyl, ($C_1$-$C_{12}$)-alkoxy, —O—[$CH_2$—]$_x$$C_fH_{(2f+1-g)}$$F_g$, —NR'R'', ($C_1$-$C_{12}$)-alkoxy-($C_1$-$C_{12}$)-alkyl, ($C_1$-$C_{12}$)-alkoxy-($C_1$-$C_{12}$)-alkoxy, ($C_7$-$C_{11}$)-aralkoxy, ($C_1$-$C_{12}$)-alkylmercapto, ($C_1$-$C_{12}$)-alkylsulfinyl or ($C_1$-$C_{12}$)-alkylsulfonyl, $R^7$ denotes a substituted ($C_6$-$C_{12}$)-aryloxy radical or ($C_7$-$C_{11}$)-araloxy radical which carries 1, 2, 3, 4 or 5 identical or different substituents selected from the group consisting of halogen, cyano, nitro, trifluoromethyl, ($C_1$-$C_6$)-hydroxyalkyl, ($C_1$-$C_6$)-alkoxy, —O—[$CH_2$—]$_x$$C_fH_{(2f+1-g)}$$F_g$, —$OCF_2Cl$, —O—$CF_2$—CHFCl, ($C_1$-$C_6$)-alkylmercapto, ($C_1$-$C_6$)-alkylsulfinyl, ($C_1$-$C_6$)-alkylsulfonyl, ($C_1$-$C_6$)-alkylcarbonyl, ($C_1$-$C_6$)-alkoxycarbonyl, carbamoyl, N-($C_1$-$C_4$)-alkylcarbamoyl, N,N-di-($C_1$-$C_4$)-alkylcarbamoyl, ($C_1$-$C_4$)-alkylcarbonyloxy, ($C_3$-$C_8$)-cycloalkyl, phenyl, benzyl, phenoxy, benzyloxy, NR'R'', phenylmercapto, phenylsulfonyl, phenylsulfinyl, sulfamoyl, N-($C_1$-$C_4$)-alkylsulfamoyl and N,N-di-($C_1$-$C_4$)alkylsulfamoyl, R' and R'' are identical or different and denote hydrogen, ($C_6$-$C_{12}$)-aryl or ($C_1$-$C_8$)-alkyl, or f is 1, 2, 3, 4, 5, 6, 7 or 8, g is 0, 1 to (2f+1), i is 1, 2, 3 or 4, n is 3 or 4, x is 0, 1, 2 or 3, or the physiologically tolerable salt thereof.

6. A compound of the formula I

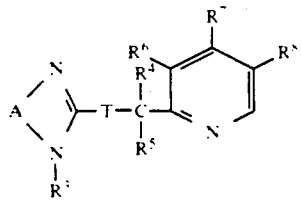

in which

A stands for

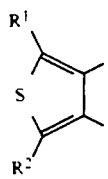

T denotes —S— or —SO—

$R^1$, $R^2$, $R^3$, $R^4$ and $R^5$ denote hydrogen or ($C_1$-$C_3$)-alkyl.

$R^6$ and $R^8$ are identical or different and denote hydrogen, ($C_1$-$C_3$)-alkyl or ($C_1$-$C_4$)-alkoxy.

$R^7$ denotes a substituted phenyloxy radical or benzyloxy radical which carries 1, 2, 3 or 4 identical or different substituents selected from the group consisting of halogen and trifluoromethyl.

or the physiologically acceptable salt thereof.

7. A compound of the formula I as claimed in claim 6, in which T stands for an —SO— group, or the physiologically acceptable salt thereof.

8. A compound of the formula I as claimed in claim 6, in which $R^7$ stands for a substituted phenylalkoxy radical of the formula

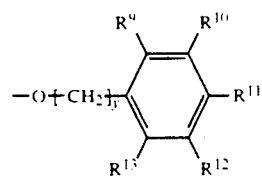

in which $R^9$, $R^{10}$, $R^{11}$, $R^{12}$ and $R^{13}$ are identical or different and denote hydrogen, halogen or trifluoromethyl, y is 0 or 1, or the physiologically acceptable salt thereof.

9. A compound of the formula I as claimed in claim 8, in which $R^7$ denotes a monosubstituted or polysubstituted benzyloxy or phenoxy radical, $R^9$, $R^{10}$, $R^{11}$, $R^{12}$ and $R^{13}$ are identical or different and denote hydrogen, fluorine, chlorine, bromine, or trifluoromethyl, and the remaining radicals and variables are unchanged, or the physiologically acceptable salt thereof.

10. A compound of the formula I as claimed in claim 1, in which Y denotes 0 or 1.

11. 2-[4-(4-trifluoromethylbenzyloxy)-2-picolyl-sulfinyl]-1H-thieno[3,4-d]imidazole, 2-[3-methoxy-4-(4-trifluoromethylbenzyloxy)-2-picolylsulfinyl]-1H-thieno[3,4-d]imidazole, 2-[3-methoxy-4-(4-fluorobenzyloxy)-2-picolylsulfinyl]-1H-thieno[3,4-d]imidazole, 2-[4-(3,5-bistrifluoromethylbenzyloxy)-2-picolylsulfinyl]-1H-thieno[3,4-d]imidazole, 2-[3-methoxy-4-(3,5-bistrifluoromethylbenzyloxy)-2-picolylsulfinyl]-1H-thieno[3,4-d]imidazole, 2-[4-(2,4-difluorophenoxy)-2-picolylsulfinyl]-1H-thieno-[3,4-d]imidazole, 2-[4-(3-trifluoromethylphenoxy)-2-picolylsulfinyl]-1H-thieno[3,4-d]imidazole, 2-[4-(4-fluorophenoxy)-2-picolylsulfinyl]-1H-thieno[3,4-d]imidazole or 2-[4-(4-chlorophenoxy)-2-picolylsulfinyl]-1H-thieno[3,4-d]imidazole or the physiologically tolerable salt thereof.

12. A pharmaceutical composition for the inhibition of gastric acid and secretion, comprising an effective amount of a compound as claimed in claim 1 or its physiologically tolerable salt and a physiologically acceptable excipient.

13. A pharmaceutical formulation for the treatment of gastrointestinal diseases containing an effective amount of a compound as in claim 1 or a physiologically tolerated salt thereof and a physiologically acceptable excipient.

14. A process for the inhibition of gastric acid secretion, which comprises the administration to a host of an effective amount of a compound as claimed in claim 1 or its physiologically acceptable salt.

15. A method for the treatment of gastrointestinal diseases, which comprises administering to a host an effective amount of a compound as claimed in claim 1 or a physiologically tolerated salt thereof.

* * * * *

UNITED STATES PATENT AND TRADEMARK OFFICE
CERTIFICATE OF CORRECTION

PATENT NO. : 5,114,955

DATED : May 19, 1992

INVENTOR(S) : Hans-Jochen Lang et al

It is certified that error appears in the above-identified patent and that said Letters Patent is hereby corrected as shown below:

In the Abstract, in the three Formulas below "A stands for", before "c)", "order" should read --or--.

Signed and Sealed this

Sixteenth Day of November, 1993

Attest:

BRUCE LEHMAN

*Attesting Officer*    *Commissioner of Patents and Trademarks*